United States Patent [19]

Kerfoot et al.

[11] 4,112,741
[45] Sep. 12, 1978

[54] SCANNING APPARATUS FOR SEPTIC EFFLUENTS

[75] Inventors: William B. Kerfoot, Falmouth; Edward C. Brainard, II, Marion, both of Mass.

[73] Assignee: Environmental Devices Corporation, Marion, Mass.

[21] Appl. No.: 828,471

[22] Filed: Aug. 29, 1977

[51] Int. Cl.$^2$ .................... G01N 21/34; G01N 27/08
[52] U.S. Cl. .................... 73/53; 73/61.1 R; 250/364; 324/65 R
[58] Field of Search .............. 73/53, 61 R, 61.1 R, 73/170 A; 324/65 R; 250/301, 361 R, 364, 365

[56] References Cited
U.S. PATENT DOCUMENTS

| | | | |
|---|---|---|---|
| 2,756,404 | 7/1956 | Anderson et al. | 73/53 X |
| 3,214,964 | 11/1965 | Davis | 73/61 R X |
| 3,250,118 | 5/1966 | Johnson, Jr. | 73/53 |
| 3,510,648 | 5/1970 | Leger, Jr. | 250/364 |
| 3,842,270 | 10/1974 | Gregory et al. | 250/365 X |
| 3,849,723 | 11/1974 | Allen | 73/61 R X |
| 3,917,945 | 11/1975 | Sema et al. | 250/301 |

OTHER PUBLICATIONS

*Counting and Recording Equipment for Coastal and Estuarine Pollution Studies,* by Briggs et al., in Proceedings of the Conference on Electronic Engineering in Ocean Technology, Sept. 1970, pp. 15–28.

Primary Examiner—Richard C. Queisser
Assistant Examiner—Joseph W. Roskos
Attorney, Agent, or Firm—Kenway & Jenney

[57] ABSTRACT

In the apparatus disclosed herein, a continuously operative sample intake is traversed along the shoreline at a preselected subsurface level appropriate for picking up effluents emanating from on-shore septic systems. The conductivity and the fluorescence of the sampled water are measured continuously, the wavelength of the fluorescence measured being chosen to determine the presence of aromatic hydrocarbons and detergent whiteners which are present in distinctive proportions in recharged septic effluents. Signal processing means are incorporated for generating an output signal which varies as a function of the conjoint deviation of the two measurements from the values thereof which are representative of background water levels.

10 Claims, 3 Drawing Figures

4,112,741

SCANNING APPARATUS FOR SEPTIC EFFLUENTS

BACKGROUND OF THE INVENTION

This invention relates to pollution detecting apparatus and more particularly to such apparatus which is useful for efficiently scanning shorelines to detect septic effluents emanating from on-shore septic systems.

Conventional surveying of a pond, inlet, or other body of water to determine the presence and sources of pollution has typically been done by collecting a large number of discrete samples at various locations within the pond and then performing chemical analyses on these samples to determine the presence of chemical components indicating pollution. Typically, in order to pinpoint a source, it has been necessary to then go back to the general area located in the initial survey and then conduct a more detailed sampling, again following the same methods. The expense of such procedures is considerable and the approach produces a large quantity of data which is not particularly useful or meaningful.

Among the several objects of the present invention may be noted the provision of apparatus for continuously scanning a shoreline to detect effluents emanated from on-shore septic systems; the provision of such apparatus which is selective for such effluents and which discriminates against natural sources of similar constituents; the provision of such apparatus which may be easily and efficiently operated; the presence of such an apparatus which continuously provides a signal correlated with or indicative of the presence of septic effluents; the provisions of such apparatus which is reliable and which is of relatively simple and inexpensive construction. Other objects and features will be in part apparent and in part pointed out hereinafter.

SUMMARY OF THE INVENTION

Briefly, apparatus according to the present invention is adapted for scanning shorelines to detect septic effluents emanating from on-shore septic systems. A continuously operable sample intake means draws water from a preselected subsurface level adjacent the shoreline and is traversed along the shoreline to provide a continuous sample flow. A fluorometer continuously measures the fluorescence of the water to determine the presence of aromatic hydrocarbons and detergent whiteners which are present in distinctive proportions in recharged septic effluents and for generating a signal which varies as a function thereof. The conductivity of the sample water is also continuously measured and a signal which varies as a function thereof is also generated continuously. Signal processing means operates on the two measurement signals to generate an output signal which varies as a function of the conjoint deviation of those signals from the values thereof which are representative of background water levels.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
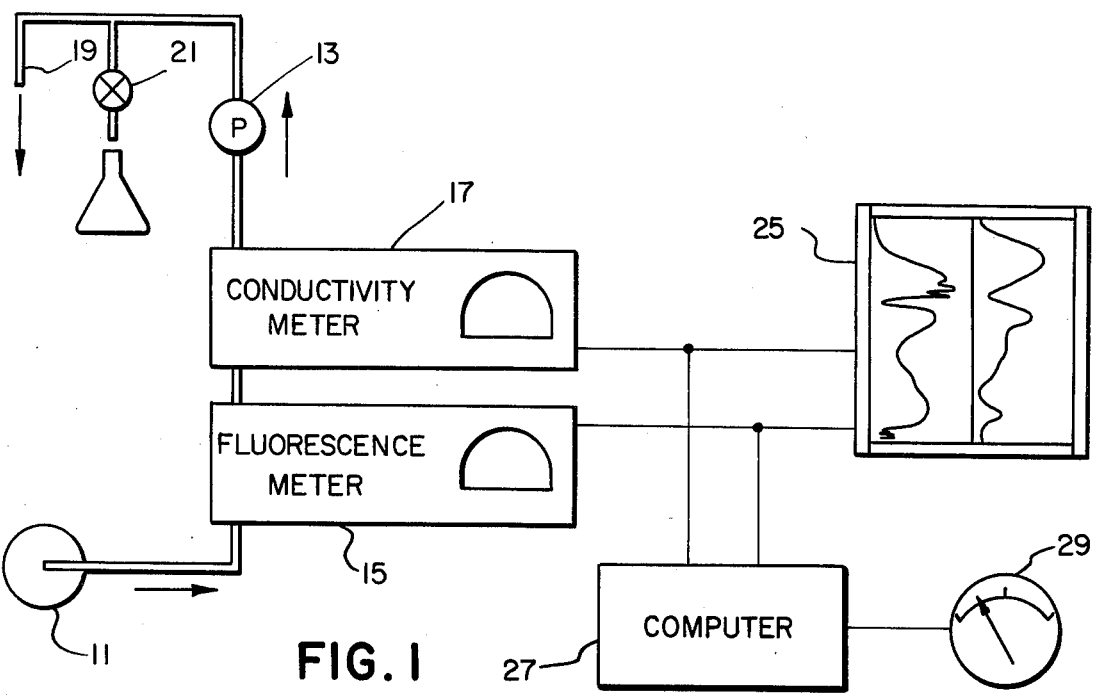
FIG. 1 is a functional block diagram of scanning apparatus according to the present invention.

In order to facilitate the scanning of the shoreline, the apparatus of the present invention is arranged so that it can be transported in a small boat, e.g. outboard engine-powered, which is then operated so as to travel along the shoreline following a preselected depth contour. A sample intake, indicated at 11 in FIG. 1, is then either towed behind the boat or held beneath the surface by means of a stiff tubular wand or pipe. The intake 11 is provided with a large spherical screen as indicated which both prevents foreign objects from entering the system and also tends to hold the inlet at a preselected distance off the bottom, the inlet being located essentially at the center of the spherical screen. The screen not only prevents the system from being clogged by bottom debris but also tends to stabilize the sensitivity of the system due to possible variation in the height off the bottom. As is understood, the water composition can vary with this height and if the operator freely controls the depth, there may be a subconcious feedback when the operator perceives a changed reading. Alternatively, the intake 11 is a downward-directed screen which limits water intake to recharged bottom water and allows screening of inflow.

Water is drawn into the inlet by a continuously operating, positive displacement pump 13, the flow passing serially through a fluorometer 15 and a conductivity meter 17. During most of the time of operation, the outlet flow from the pump is merely discharged over the side of the boat, as indicated at reference character 19. However, a tap and valve are provided along the outlet line, as indicated at 21, so that discrete samples may be drawn off the flow at any desired intervals, i.e. to enable a subsequent more detailed chemical analysis of the water being sampled.

In one particular embodiment of the invention, the fluorometer 15 was a Series 10 Fluorometer manufactured by the Turner Designs Company and the conductivity meter was a Balsbaugh Series 900 conductivity meter. Each of the measuring devices 15 and 17 provides a continuous signal which varies as a function of the measured parameter. In the case of the conductivity meter 17, the signal is simply a voltage which varies essentially directly as a function of conductivity whereas the fluorometer provides a voltage signal which varies as a function of the fluorescence of the sample water at selected excitation and measurement wavelengths. Both the conductivity measurement signal and the fluorescence measurement signal with appropriate temperature compensation are applied to a strip chart recorder 25 which makes a continuous record of these values, i.e a record suitable for subsequent study and analysis.

The excitation and measurement wavelengths employed in shoreline scanning in accordance with the teachings of the present invention are selected so as to determine the presence of aromatic hydrocarbons and detergent whiteners which are present in distinctive proportions in recharged septic effluents, that is, septic effluents which have passed a substantial distance through soil of the character abutting the shoreline. Excitation in the order of 350–390 nm is appropriate as is emission measurement in the range of 400–450 nm.

The presently preferred excitation wavelength is 360 nanometers and the preferred emission measurement wavelength range is 400-440 nanometers. These wavelengths are chosen in that they correspond to a peak in the characteristic fluorescence spectrum of recharged septic effluent which does not correspond to a peak in naturally occurring ground waters, e.g. a runoff from peaty soils which includes somewhat similar fluorescent constituents.

As is described in greater detail hereinafter, both of the measured parameters tend to vary from their nominal values when the intake is traversed through a discharge plume constituting effluent emanating from an on-shore septic system. In order to provide an immediate, reliable indication of such a plume, the apparatus of the present invention incorporates signal processing means, indicated at 27 in the drawing of FIG. 1, which operates to provide an output signal which is a function of the conjoint deviations of the two measurement signals from the values which are representative of the background water. This output signal is indicated directly on a meter 29. Provision may also be made for recording this signal, as with the two, direct measurement signals.

Figure 2:
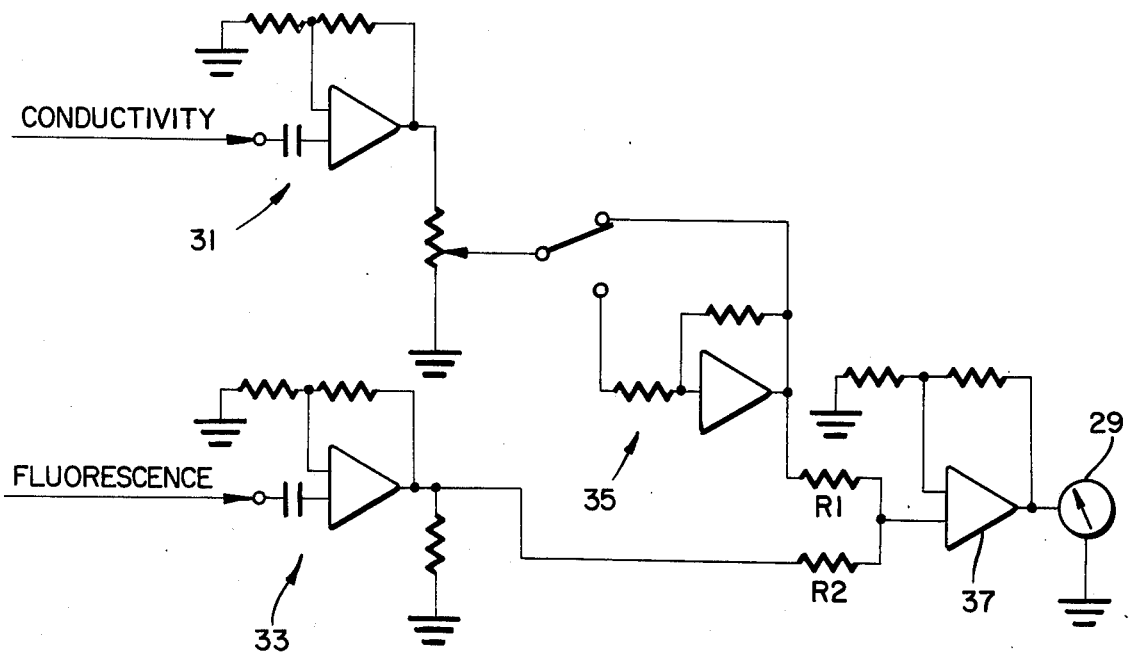
FIG. 2 is a schematic cicuit diagram of signal processing means employed in the apparatus of FIG. 1.

With reference to the FIG. 2 circuit diagram, the conductivity signal and the fluorescence signal are each first applied to respective rate amplifiers 31 and 33. These rate amplifiers operate to block the d.c. components of the conductivity and fluorescence signals, thereby effectively eliminating that portion of each signal which is representative of the background water contribution to the respective measurement. Thus, the output signals from these amplifiers are indicative of changes in the respective measurements rather than their absolute levels. Accordingly, the time constants of the rate amplifiers are selected so as to be commensurate with the time constants of the measurement systems and the rate at which the system will be scanned along the shoreline. In general, time constants in the order of 100 to 1000 seconds have been found appropriate since an aliquot of water will pass through the system in about 3 to 5 seconds and the boat is preferably traversed at about 1.0 to 2.0 feet per second.

As is understood by those skilled in the art, a discharge plume from an on-shore septic system will cause an increase in conductivity when flowing into fresh water but will cause a decrease in conductivity when flowing into salt or brackish water. Accordingly, an inverter circuit 35 is provided which may be selectively introduced or omitted from the path of the conductivity signal, i.e. to accommodate for this reversal in the effect of the sensed parameter.

In order to provide an output signal which varies as a function of the conjoint deviation of the two measurement signals from the values thereof which are representative of background water levels, the two signals are applied, through respective weighting resistors $R_1$ and $R_2$, to a summing amplifier 37. The output signal from this amplifier constitutes the output signal from the system and is applied directly to the meter 29 so as to provide a direct and immediate indication of pollution index.

The apparatus of the present invention is particularly efficient and useful in quickly locating the source of septic effluents in that it senses two parameters which are affected by a septic discharge plume and operates to provide an indication which varies as a function of the conjoint deviation of those two parameters from normal levels. A numerical example may be useful in understanding this operation, the example being based on a particular chemical analysis, carbon chloroform extract (CCE), which corresponds or correlates well with the fluorometric measurement being performed by the apparatus of the present invention. The CCE measurement for background water in a particular instance might be 0.5 milligrams per liter and the conductivity might be 52 micromhos per centimeter. In contrast, the CCE measurement for recharged septic effluent might typically be in the order of 3.5 milligrams per liter and the conductivity (C) 300 micromhos per centimeter. It is important to note that the values considered are those corresponding to the recharged effluent rather than the secondary effluent as it leaves the septic system. In accordance with one aspect of the present invention, it has been determined that the chemical charactertistic of the septic leachate changes as it passes a significant distance through soil but then reaches a fairly stable composition. It is to this fairly stable composition that the sensing parameters of the present apparatus are preferably adjusted thereby to obtain maximum sensitivity for the septic effluents while obtaining maximum discrimination against naturally occurring ground water constituents.

Figure 3:
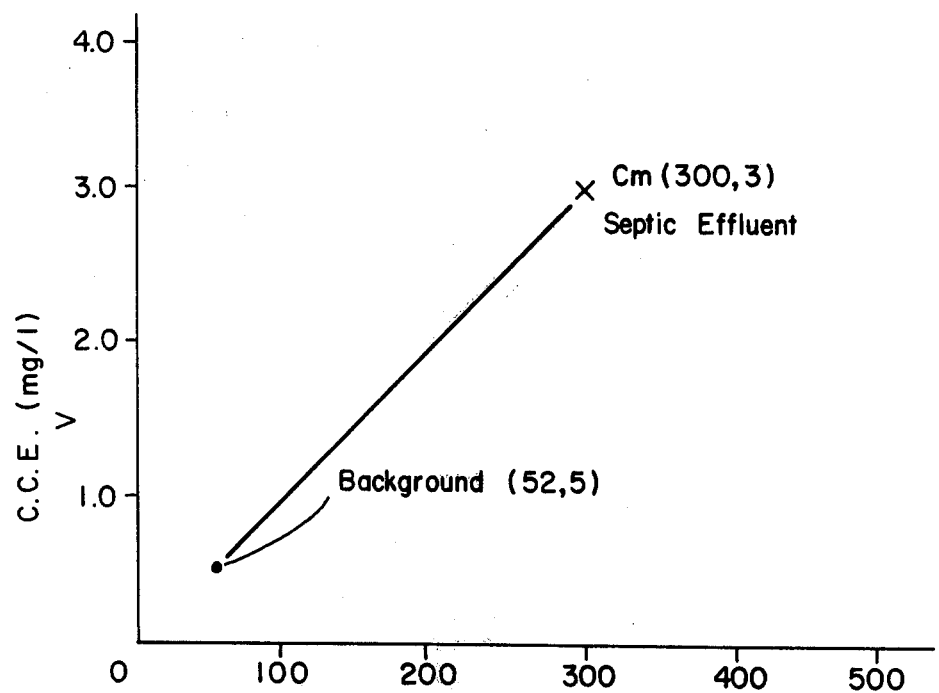
FIG. 3 is a graph illustrating the technique of numerical taxonomy which is approximated by the signal processing means of FIG. 2.

In FIG. 3, the two points representing the background water and the recharged effluent are indicated on the graph. As will be understood by those skilled in the art, mixtures of these two compositions would then provide values lying along a line connecting the two points. However, the unavoidable presence of other components and variations of the septic effluent and the ground water composition make such an exact prediction impossible. It is, however, desirable to in some way provide an indication of the degree of pollution. Using a technique employed in numerical taxonomy, the similarity of a class of water can be expressed as the ratio $(k)$:

$$k = \frac{C.C.E._o - C.C.E._{bk}}{\frac{C_o C_{bk}}{C_E FF - C_{bk}} (C.C.E._{EEF} - C.C.E._{bk})} = \frac{.6 - .5}{\frac{250 - 52}{300 - 52}(3 - .5)} = .05$$

where only positive (+) values are accepted. If a greater number of constituents are used, the taxonomic distance formular can be used:

$$k^2 = \frac{(C.C.E._o - C.C.E._{bk})^2}{(C.C.E._{EFF} - C.C.E._{bk})^2} + \frac{(C_o - C_{bk})^2}{(C_{EFF} - C_{bk})^2}$$

where $$k = \sqrt{\frac{(C.C.E._o - C.C.E._{bk})^2}{(C.C.E._{EEF} - C.C.E._{bk})^2} + \frac{(C_o - C_{bk})^2}{(C_{EFF} - C_{bk})^2}}$$

if more than two constituents are considered:

$$k = \sqrt{\frac{(X_o - X_{bk})^2}{(X_{EFF} - X_{bk})^2} + \frac{(Y_o - Y_{bk})^2}{(Y_{EFF} - Y_{bk})^2} + \frac{(Z_o - Z_{bk})^2}{(Z_{EFF} - Z_{bk})^2}}$$

where:

$C.C.E._{EFF}$ = concentration of fluorescent equivalent of the carbon chloroform extract unique to reference wastewater effluent (mg/l);

C.C.E.$_{bk}$ = background concentration in surface water body of fluorescent equivalent of the carbon chloroform extract unique to wastewater effluent (mg/l);

C.C.E.$_o$ = observed concentration in recharged water of fluorescent equivalent of the carbon chloroform extract unique to wastewater effluent (mg/l);

C$_{bk}$ = background conductivity in surface water body (mg/l);

C$_o$ = conductivity of observed recharge water;

C$_{EFF}$ = conductivity of reference wastewater effluent; and k = coefficient of similarity.

The larger the number of constituents monitored simultaneously, the higher the certainty that the analyzed water is "effluent" and not just a coincidental background fluctuation. In practice, only a pair of the most significant constituents are continually monitored, with water samples taken at the peak concentrations incidating "effluent" for later confirmation by follow-up chemical analyses.

To yield the effluent equivalent fraction in absolute concentrations, the equivalent fraction coefficient (k) is used as an additional coefficient in a standard regression equation describing a calibration series based upon known quantities of "standard effluent" added to the natural background water.

$$y = a(k) x + b$$

If "standard effluent" is used for calibration, k = 1 and the calibration curve represents the concentration of effluent present in the water. With the equation, x equals the concentration of reference effluent (in mg/l), a the slope of the line, b the intercept, y the amplitude of the modulated signal (in relative effluent units).

While the simple summing amplifier circuitry employed in the signal processor apparatus circuitry shown in FIG. 2 provides only a first level aproximation of this function, it is sufficiently useful in the context of quickly locating sources of septic pollution. It should, however, be understood that more elaborate signal processing could also be provided and means might also be incorporated for measuring a third parameter so that the statistical likelihood of pinpointing septic sources as distinguished from natural sources could be increased. The use of the two parameters disclosed, however, have been found to be an admirable compromise between speed and accuracy.

In actual practice, it has been found advantageous to scan the shoreline using the apparatus of FIG. 1 and, when a source of pollution is indicated by the meter 29, to then take a plurality of discrete samples for later chemical analysis. This analysis is preferably for nutrients NO$_3$—N, NH$_4$—N, PO$_4$—P. The detailed chemical analyses then provides a highly precise pinpointing of the nature and contribution of the several possible sources of the change in indication while the use of the apparatus of the present invention means that the total number of samples so collected and analyzed is reduced by at least an order of magnitude over that which would be required to survey an equivalent body of water.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Apparatus for scanning shorelines to detect septic effluents emanating from on-shore septic systems; said apparatus comprising:

continuously operable sample intake means for drawing water from a preselected subsurface level adjacent the shoreline, said means being traversable along the shoreline;

a fluorometer for continuously measuring the fluorescence of the sampled water to determine the presence of aromatic hydrocarbons and soap whiteners which are present in distinctive proportions in recharged septic effluents and for generating a signal which varies as a function thereof;

conductivity measuring means for continuously measuring the conductivity of the sample water and for generating a signal which varies as a function thereof; and signal processing means for generating an output signal which varies as a function of the conjoint deviation of said measurement signals from the values thereof which are representative of background water levels.

2. Apparatus as set forth in claim 1 wherein said signal processing means includes a rate amplifier in the input channel for each of said measurement signals.

3. Apparatus as set forth in claim 2 wherein said rate amplifiers have time constants in the order of 100–1000 seconds.

4. Apparatus as set forth in claim 1 wherein said signal processor includes means for selectively reversing the polarity of said conductivity measurement signal.

5. Apparatus as set forth in claim 1 wherein said sample intake means includes an inlet and means for spacing said inlet a preselected distance from the offshore bottom.

6. Apparatus as set forth in claim 5 wherein said spacing means comprises an essentially spherical screen around said inlet.

7. Apparatus for scanning shorelines to detect septic effluents emanating from on-shore septic systems; said apparatus comprising:

continuously operable sample intake means for drawing water from a preselected subsurface level adjacent the shoreline, said means being traversable along the shoreline;

a fluorometer for continuously measuring the fluorescence of the sampled water by applying excitation energy in the range of 350–390 nm and by measuring emission in the range of 400–450 nm to determine the presence of constituents which are present in distinctive proportions in recharged septic effluents and for generating a signal which varies as a function thereof;

conductivity measuring means for continuously measuring the conductivity of the sample water and for generating a signal which varies as a function thereof; and signal processing means for generating an output signal which varies as a function of the conjoint deviation of said measurement signals from the values thereof which are representative of background water levels.

8. The method of determining the relative condition of a body of water adjacent a shoreline as affected by shoreside wastewater systems, said method comprising:
  (a) a continuous sampling of water within the shallow boundary zone near the bottom of the body of the water to obtain components including groundwater seepage;
  (b) a continual analysis of the concentration of fluorescent organics such as aromatic hydrocarbons excited in the range of 350-390 nm and emission recorded in the range 400-450 nm;
  (c) simultaneously analyzing the difference in conductivity of the bottom seepage compared to the natural background of the water body;
  (d) simultaneously computing the correspondence of the magnitude of the ratio of the two signals as compared with a standard secondary effluent, thereby to determine the location and approximate surface dimensions of a plume emerging from the bottom sediments caused by the volume of discharge from an on-shore wastewater system; and
  (e) taking and chemically analyzing discrete samples of the water found at the peak concentration of the suspected wastewater constituents for the nutrients $NO_3$—N, $NH_4$—N, $PO_4$—P.

9. The method as set forth in claim 8 wherein said sampling is accomplished using means for maintaining an intake inlet a predetermined height off the bottom.

10. The method as set forth in claim 9 wherein said means comprises a spherical screen around the end of an inlet tube.

* * * * *